United States Patent [19]

Tabor et al.

[11] 4,395,395

[45] Jul. 26, 1983

[54] DETECTION OF NON-A, NON-B HEPATITIS ASSOCIATED ANTIGEN

[75] Inventors: Edward Tabor, Rockville; Robert J. Gerety, Potomac, both of Md.

[73] Assignee: The United States of America as represented by the Department of Health and Human Services, Washington, D.C.

[21] Appl. No.: 319,995

[22] Filed: Nov. 10, 1981

Related U.S. Application Data

[63] Continuation-in-part of Ser. No. 192,291, Sep. 30, 1980, abandoned, which is a continuation-in-part of Ser. No. 40,921, May 21, 1979, Pat. No. 4,356,146.

[51] Int. Cl.³ .................. A61K 39/12; C07G 7/00; A61K 37/00
[52] U.S. Cl. ................ 424/89; 260/112 R; 424/177
[58] Field of Search ............ 424/89, 177; 260/112 R

[56] References Cited

U.S. PATENT DOCUMENTS

| | | | |
|---|---|---|---|
| 3,143,474 | 8/1964 | Froelich | 424/89 |
| 3,636,191 | 1/1972 | Blumberg et al. | 424/89 |
| 3,636,196 | 1/1972 | Bauer et al. | 424/89 |
| 3,790,552 | 2/1974 | Johnson et al. | 424/89 |
| 3,994,870 | 11/1976 | Newrath et al. | 424/89 |
| 4,013,411 | 3/1977 | Shupack et al. | 424/89 |
| 4,017,360 | 4/1977 | Bertland et al. | 424/89 |
| 4,017,601 | 8/1977 | Hilleman et al. | 424/89 |
| 4,029,764 | 6/1977 | Provost et al. | 424/89 |
| 4,031,203 | 6/1977 | Provost et al. | 424/89 |
| 4,057,628 | 11/1977 | Bick | 424/89 |
| 4,087,519 | 5/1978 | Trepo | 424/89 |
| 4,102,996 | 7/1978 | McAleer et al. | 424/89 |
| 4,113,712 | 9/1978 | Funakoshi | 424/89 |
| 4,118,477 | 10/1978 | McAleer et al. | 424/89 |
| 4,118,478 | 10/1978 | Prince et al. | 424/89 |
| 4,138,287 | 2/1979 | Anderson et al. | 429/89 |
| 4,164,566 | 2/1979 | Provost et al. | 424/89 |
| 4,186,193 | 1/1980 | McAleer et al. | 424/89 |
| 4,234,564 | 11/1980 | McAleer et al. | 424/89 |
| 4,242,324 | 12/1980 | McAleer et al. | 424/89 |

OTHER PUBLICATIONS

The Lancet, Jul. 14, (1979), p. 92.
The Lancet, (1970), vol. 101, pp. 1031-1032.
The Lancet, (1978), 853-856.
Vyas et al., Viral Hepatitis, (1978), 419-421.
The Lancet, (1978), 463-466, (1-6).
Gastroenterology, (1979), 76, 660-664.

*Primary Examiner*—Delbert R. Phillips
*Attorney, Agent, or Firm*—John S. Roberts, Jr.

[57] ABSTRACT

In the detection of the highly transmittable agent of non-A, non-B hepatitis there is described a method utilizing antigen-antibody reaction and preferred counterelectrophoresis method for the detection of said antigen. This method may also be applied to producing a vaccine.

4 Claims, No Drawings

DETECTION OF NON-A, NON-B HEPATITIS ASSOCIATED ANTIGEN

CROSS-REFERENCE TO RELATED APPLICATION

This application is a continuation-in-part of copending application Ser. No. 192,291, filed Sept. 30, 1980 now abandoned, which is a continuation-in-part of pending Ser. No. 040,921, filed May 21, 1979, U.S. Pat. No. 4,356,146 issued Oct. 26, 1982.

INTRODUCTION

The present invention is concerned with the discovery of the existence of a non-A, non-B hepatitis associated antigen and this invention is also concerned with the use of this antigen and/or its antibody to identify infectious blood donors and to prepare a vaccine. It is realized that in the time span after the discovery of the existence by the present inventors, there appeared an article by Shirachi et al, "Hepatitis 'C' Antigen in Non-A, Non-B Post-Transfusion Hepatitis," The Lancet, Oct. 21, 1978, pages 853–856.

In recent studies non-A, non-B hepatitis has been found to occur in 10% of transfused patients in the United States, resulting in about 200,000 cases per year. Fatalities from non-A, non-B hepatitis in the United States probably number around 1,000 per year among transfusion-related cases.

PRIOR ART STATEMENT

Shirachi et al, The Lancet, Oct. 21, 1978, pages 853–856.

Tabor et al, Viral Hepatitis, eds. G. N. Vyas et al, The Franklin Institute Press, Philadelphia, 1978, pages 419–421.

Tabor et al, The Lancet, Mar. 4, 1978, pages 463–466.

Tabor et al, Gastroenterology, 76:680–684, 1979.

Gocke et al, The Journal of Immunology, 104(4): 1031–1032, April, 1970.

THE NON-A, NON-B ANTIGEN AND ITS ANTIBODY

Many cases of acute and chronic hepatitis which do not result from infection by either hepatitis A virus (HAV) or hepatitis B virus (HBV), are called "non-A, non-B hepatitis," and now account for 89% of cases of post-transfusion hepatitis in the United States. The presence of a transmissable agent in this disease has been demonstrated by its transmission to chimpanzees by the inoculation of serum from humans chronically infected with non-A, non-B hepatitis, and by serial passage to additional chimpanzees. An antigen-antibody system detected by agar gel diffusion and counter-electrophoresis (CEP) was described in humans with post-transfusion non-A, non-B hepatitis (Shirachi, et al, supra). In the present invention is reported antigen which is detectable by CEP in the serum of chimpanzees during the acute phase of experimentally induces human non-A, non-B hepatitis, an antibody which appears during convalescence, and the detection of this antigen-antibody system in humans with non-A, non-B hepatitis.

The activity of the antigen has been shown in counterelectrophoresis (CEP) as well as in a solid phase radioimmunoassay.

Additionally, human tests showed antigen activity persisted in serum up to six years in chronically infected humans whose blood had transmitted this disease. The tests enable blood banks to identify blood donors whose blood may transmit non-A, non-B hepatitis to recipients and eliminate the use of their blood for transfusion. This will result in a decrease in the incidence of this disease. The test is also used to diagnose non-A, non-B hepatitis in patients.

An antigen was detected by counterelectrophoresis in serum samples from six to seven chimpanzees during the acute phase of experimentally induced non-A, non-B hepatitis using antiserum from a chimpanzee convalescent from human non-A, non-B hepatitis. This antigen could not be detected prior to the transfusion in 35 pre-inoculation serum samples from these chimpanzees, or in 94 weekly bleedings from three chimpanzees with hepatitis A and three chimpanzees with hepatitis B.

The antigen was also detected in each of four serum samples obtained from a human with chronic hepatitis whose blood had transmitted non-A, non-B hepatitis to a nurse by accidental needlestick and to chimpanzees by experimental inoculation. The antigen was also detected in two of two additional human sera which had transmitted non-A, non-B hepatitis to humans and chimpanzees. In addition, the antigen was detected in serum obtained retrospectively from 11 of 31 former blood donors whose blood had transmitted post-transfusion non-A, non-B hepatitis several years previously to recipients of a single unit of their blood.

Antibody to this antigen was detected in convalescent serum samples from all seven chimpanzees studied, in convalescent serum from the nurse infected by accidental needlestick, in serum from a hemodialysis patient convalescent from non-A, non-B hepatitis, and in six of the implicated blood donors.

COUNTERELECTROPHORESIS

Counterelectrophoresis (CEP) which may be also described as immunoelectroosmophoresis (IEOP) or immunoelectrodiffusion (IED) or countercurrentelectrophoresis is utilized as follows.

Sera stored at −20° C. were tested by CEP using 1% agarose (Indubiose A37, L'industrie Biologique Francaise, Gennevilliers, France) in barbital buffer, pH 8.6, poured onto 3.5×12.5 cm glass plates (16 ml per plate). Melted agarose (16 ml) was poured onto a lantern slide. When it had cooled, two rows of holes were punched in the agarose. Antibody was placed in one row of holes and samples to be tested for antigen were added to the other row. When testing for antibody, antigen was added to one row and samples in the other row. The lantern slide was placed in a CEP chamber. Paper wicks were used to connect each side of the slide to each of two pools of barbital buffer, pH 8.6. An electric current was passed across the plate, 35 milliamps per plate, for one hour. Immunoprecipitin lines were read after 1, 24, and 48 hours of storage in a moist chamber at room temperature. When the test sample was positive, a precipitin line was seen between the rows, using the naked eye with the aid of an electric lamp.

RADIOIMMUNOASSAY (RIA)

Antibody to the non-A, non-B hepatitis was purified by precipitating it from serum using 30% ammonium sulfate. This purified antibody was labeled with radioactive iodine using the chloramine-T method. Unpurified antibody was coated on plastic beads. The coated beads were placed in wells of a plastic plate. Samples to be tested for antigen were added to each well. After 18 hours incubation, the excess sample (other than any antigen which was then attached to the bead) was washed away. The radio-labeled purified antibody was then added to the wells and incubated for three hours; the excess was washed away. The amount of radioactivity adhering to the beads was counted in a gamma counter. Positive results were identified by the detection of radioactivity on the beads, in comparison to negative samples. The presence of antibody was determined by adding the sample to be tested to a known antigen-positive serum, and then, following incubation for one hour, testing the mixture for antigen. The presence of antibody was identified by the decrease in radioactive counts compared to the result obtained using the antigen alone (diluted to the same extent as the incubated mixture).

Similarly, the radioimmunoassay for detection of the antibody could be in the form of a direct radioimmunoassay. Such a method would be similar to that described above for the detection of antibody but would involve coating the plastic beads with unpurified antigen, adding the test sample, and adding radio-labeled purified antigen in the final step.

In addition to CEP and RIA used to detect antigen and antibody, alternate immunological methods may be used to detect the antigen and antibody including agar gel diffusion, passive hemagglutination, latex agglutination, complement fixation, and enzyme-linked immunosorbent assay. Either a direct or a competitive inhibition type assay could be used to detect the antibody with any of these methods.

THE ANTIGEN

An abbreviated or capsulized description of purification for the associated antigen and active subunits is summarized as follows.

The non-A, non-B hepatitis associated antigen was purified from serum (or from other tissues such as liver, or tissue and cell cultures when the agent is propagated) by selection from the following techniques:

(1) Fractional (selective) precipitation or solubilization;

(2) Gel filtration, molecular sieving;

(3) Chromatographic techniques (affinity, adsorption or ion-exchange chromatography);

(4) Density gradient centrifugation;

(5) Electrophoresis including isotachophoresis and isoelectric focusing;

(6) Countercurrent distribution.

Further purification treatments include alterations in pH, chemical treatments and enzyme treatments.

Subunits

Immunologically active subunits of the non-A, non-B hepatitis associated antigen have been prepared following preliminary purification of the antigen by a selection from the following:

(1) detergent treatment
(2) limited hydrolysis
(3) reduction

Immunologically active polypeptides have been separated here by procedures outlined above.

Development of In Vitro Tests

By inducing antibody specific for the non-A, non-B associated antigen in suitable animal species or selecting human sera containing these antibodies, immunologic tests to detect the antigen (such as agar gel diffusion, counterelectrophoresis, later agglutination, complement fixation, passive hemagglutination, radioimmunoassay or enzyme-linked immuno-sorbent assay) have been developed and used to (1) detect persons transmitting non-A, non-B hepatitis and (2) identify sources of antigen for in vitro tests and vaccine production.

Vaccine

A direct use of purified antigen or immunologically active subunits inactivated by either heat, formalin or both, or attenuated, may be conventionally utilized as a vaccine.

This vaccine is effective against non-A, non-B hepatitis infection in mammals and comprises an inactive or attenuated agent or an antigen therefrom as isolated from a specimen of blood serum, tissue or a cell culture of a donor mammal known to be infected with non-A, non-B hepatitis. Such a vaccine additionally may be entitled to comprise a non-infectious immunologically active polypeptide isolated from specimens of blood serum, liver, or other tissue, tissue culture or a cell culture of a donor mammal known to be infected with non-A, non-B hepatitis as shown above. This vaccine may be used in a chimpanzee or a human being. Further, this invention includes a method of vaccination against non-A, non-B hepatitis in mammals comprising injection of an immunologically effective amount of a vaccine as in a human being.

Such a method of preparation of the antigen is described as purifying the antigen before being inactivated by the technique of fractional precipitation followed by solubilization and gel filtration and molecular sieving and affinity, adsorption or ion exchange chromatography and desnity gradient centrifugation and electrophoresis or countercurrent distribution. In the above, the antigen may be further purified by utilizing at least one of the following treatments, alteration in pH or chemical treatment or enzyme treatment. Thus, in the present invention there is a method of preparing a vaccine effective against non-A, non-B hepatitis infection in mammals which comprises isolating the antigen associated with the hepatitis from specimens of blood serum, liver or other tissue, tissue culture or a cell culture taken from a donor mammal known to be infected with non-A, non-B hepatitis, then preliminarily purifying the antigen, the separating immunologically active polypeptides from the antigen by detergent treatment, limited hydrolysis or reduction and inactivating said immunologically active polypeptide.

The Table below shows a summary of clinical testing.

TABLE 1

| Patients Tested | Non-A, Non-B Antigen | Antibody |
|---|---|---|
| 54 Normal volunteer blood donors | 0 | Not tested |
| 3 Humans with chronic non-A, non-B hepatitis who transmitted the disease to humans and chimpanzees | 3 | 0 |
| 31 Blood donors who transmitted non-A, non-B hepatitis one to four years previously | 11 | 5 |
| 12 Humans with non-A, non-B hepatitis (weekly samples) | 8 | Not tested |
| 2 Humans who recovered from non-A, non-B hepatitis | 0 | 2 |

TABLE 1-continued

| Patients Tested | Non-A, Non-B Antigen | Antibody |
|---|---|---|
| 152 Hemophiliac patients | Not tested | 59 |

EXAMPLE 1

Serum samples were obtained from three humans with chronic non-A, non-B hepatitis. Blood from human #1 had caused non-A, non-B hepatitis in a nurse who accidentally cut herself on a piece of glass contaminated with his blood. Humans #2 and #3 had donated blood, and their blood had caused non-A, non-B hepatitis in recipients. Serum from all three (humans #1, #2, and #3) was inoculated into chimpanzees and caused non-A, non-B hepatitis in the chimpanzees. The non-A, non-B hepatitis associated antigen was found in the blood of all three humans.

EXAMPLE 2

Serum samples were obtained from 31 blood donors whose blood had caused non-A, non-B hepatitis in patients who had been transfused with a single unit of their blood (and no other blood) one to four years previously. The non-A, non-B hepatitis associated antigen was detected in 11 of these donors.

EXAMPLE 3

Serum was tested from 54 normal blood donors. None had the non-A, non-B hepatitis associated antigen.

EXAMPLE 4

Five of the 31 implicated blood donors (confer Example 2) had antibody to the non-A, non-B associated antigen, but no detectable antigen. The antibody in the cases indicated the presence of a different stage of disease and was also an indication that in some cases their blood would transmit the disease, as it had done previously.

EXAMPLE 5

Chimpanzee Studies

Weekly serum samples from seven chimpanzees beginning four weeks before inoculation with human non-A, non-B hepatitis were tested. The inoculation and course of infection in these chimpanzees are described in the three Tabor et al articles noted in the Prior Art Statement, supra. Each chimpanzee was infected by intravenous inoculation of serum from one of three humans chronically infected with non-A, non-B hepatitis. Chimpanzees #922, #930, #911, #916, and #946 were infected by inoculation with Inoculum I, or with acute phase serum from a chimpanzee infected by Inoculum I (Inoculum I passage). Chimpanzee #918 was infected by Inoculum II and #919 by Inoculum III. A convalescent serum from each chimpanzee was used as antibody in CEP against that chimpanzee's own weekly serum samples; in three chimpanzees (#922, #918, #919), the convalescent serum was obtained after two intravenous inoculations with infectious serum. In addition, convalescent serum from chimpanzee #922 was used to test all chimpanzee serum samples studies.

Results. The antigen was detected in the sera of six of seven chimpanzees during non-A, non-B hepatitis. In general, the antigen was detected during the time of elevated aminotransferase levels but without a strict correlation with histopathologic changes in liver biopsy specimens. Chimpanzee #922 (Inoculum I) had elevated aminotransferase levels from Week 2 to 16 and had antigen detectable at Weeks 4–9 and at Week 15. Chimpanzee #930 (Inoculum I) had elevated aminotransferase levels from Week 3 to 23 and had antigen detectable at Weeks 2–8 (including two serum samples shown to transmit non-A, non-B hepatitis to experimentally inoculated chimpanzees) and at Week 18. Chimpanzee #911 (Inoculum I passage) had elevated aminotransferase levels from Week 5 to 21 and had antigen detectable at Weeks 19 and 20. Chimpanzee #946 (Inoculum I passage) had elevated aminotransferase levels from Week 3 to 11 and had antigen detectable at Weeks 9, 10, 12, and 16. Chimpanzee #918 (Inoculum II) had elevated aminotransferase levels from Week 4 to 20 and had antigen detectable at Weeks 6, 11, 14, and 15. Chimpanzee #919 (Inoculum III) had elevated aminotransferase levels from Week 3 to 20 and had antigen detectable at Week 3. The antigen could not be detected in serum samples from Chimpanzee #916 (Inoculum I passage).

The antigen could not be detected in any of 35 pre-inoculation serum samples from these chimpanzees, nor could it be detected in 28 weekly bleedings from three chimpanzees during experimentally induced hepatitis A or in 66 weekly bleedings from three chimpanzees during experimentally induced hepatitis B.

Antibody was detected in convalescent serum samples from all seven chimpanzees. Antibody was detected in every serum sample from chimpanzee #922 beginning with Week 28 after inoculation, 13 weeks after the disappearance of antigen and the return of aminotransferase levels to near normal values. Antibody remained detectable until longer than 19 months after inoculation. Titrations performed on selected serum samples from chimpanzee #922 before and after a second intravenous exposure to a non-A, non-B hepatitis inoculum (Inoculum III), revealed a four-fold increase in antibody titer. Ammonium sulfate precipitation and DEAE cellulose chromatography revealed the antibody to be in the 7S (IgG) fraction, although it may also be present in other globulin fractions as well in certain sera.

EXAMPLE 6

Human serum used as antibody in CEP included convalescent serum from the nurse who had recovered from non-A, non-B hepatitis 4 years earlier after the needlestick exposure to Inoculum I and convalescent serum from a multiply-transfused hemodialysis patient with a history of non-A, non-B hepatitis. The antibody was detected in convalescent serum from these humans. Antibody was not detected in any of four serum samples from the patient with chronic non-A, non-B hepatitis whose serum became Inoculum I.

EXAMPLE 7

An agent of human non-A, non-B hepatitis was shown to be present in the serum of an experimentally infected chimpanzee by transmission of the disease to five additional chimpanzees by inoculation of 0.1 to 1.0 ml of this serum, including two inoculated subsequent to the present invention. Samples of this serum (0.1 ml each) were incubated with 1:1000 formalin at 37° C. for 96 hours. Three colony-born infant chimpanzees were then inoculated with this formalin-treated serum; one received a single intravenous inoculation and two received two subcutaneous inoculations one month apart. A fourth uninoculated chimpanzee served as a control. None developed recognizable non-A, non-B hepatitis during seven months of observation, as judged by normal aminotransferase levels in weekly serum samples, normal liver histology in bi-weekly liver biopsies, and the absence of the recently reported non-A, non-B hepatitis associated antigen and antibody in their sera. All four chimpanzees remained susceptible to non-A, non-B hepatitis when subsequently challenged with 0.1 ml of untreated serum 31 weeks after the initial inoculations. Thus, an inactive vaccine was produced which was shown to be non-infectious; too little antigen was used in this study to induce protective immunity, although such immunity would be produced by use of a larger concentration of antigen.

EXAMPLE 8

Supplementary studies to Example 7 showed that a vaccine could be made to protect against non-A, non-B hepatitis in this case with sufficient antigen and starting material using undiluted Inoculum I (cf. Example 6) containing the same agent as in the $10^{-1}$ dilution of Inoculum Ip2W4 of Example 7 but in ten times the concentration. This inoculum and its derivatives were shown to transmit non-A, non-B hepatitis to 30 chimpanzees.

Two one ml aliquots of this inoculum were diluted to a final volume of 10 ml in phosphate-buffered saline, pH 7.4, in order to prevent polymerization of albumin in the serum during heating. Each sample was heated at 60° C. for 10 hours while monitoring the temperature in a control vial at 20-minute intervals. Each sample was then inoculated intravenously into one of two colony-born infant chimpanzees with no prior exposure to blood or plasma derivatives. Aminotransferase levels remained within normal limits in weekly serum samples, and no evidence of hepatitis was detected in liver biopsy specimens obtained at one- to two-week intervals during six months of evaluation.

The above data showed that the agent in Inoculum I is susceptible to inactivation by heating at 60° C. for 10 hours. In this study, the effect of dilution of the inoculum alone was not evaluated, but this was not important since the entire volume (after dilution) was injected into each chimpanzee. Another method to prevent polymerization of albumin instead of dilution is the addition of sodium caprylate and N-acetyl tryptophan.

Subsequently, studies were conducted to determine whether these chimpanzees were protected by this vaccine. Each was inoculated intravenously with one ml of unheated Inoculum I. One chimpanzee was completely protected against non-A, non-B hepatitis. Aminotransferase levels remained completely normal in weekly serum samples. Liver biopsies obtained every other week showed no evidence of hepatitis. The other chimpanzee was partially protected, with aminotransferase levels normal each week except for mild elevations (peak ALT 61 IU/1) during four weeks, with abnormal liver biopsies. These changes were much milder than seen following inoculations of this Inoculum in unvaccinated chimpanzees. Thus, the vaccination with the material containing a greater concentration of antigen protected against non-A, non-B hepatitis: completely protected one chimpanzee and modified the disease in the second chimpanzee.

We claim:

1. A vaccine effective against non-A, non-B hepatitis infection in mammals comprising an antigen isolated from a specimen of blood serum or liver tissue which has been shown to transmit non-A, non-B hepatitis.

2. A vaccine according to claim 1 in which the antigen or agent has been purified after isolation.

3. A vaccine according to any of claims 1 or 2 wherein the donor mammal is a chimpanzee.

4. A vaccine according to any one of claims 1 or 2 wherein the donor mammal is a human being.

* * * * *